United States Patent
Aoki et al.

(10) Patent No.: US 10,836,923 B2
(45) Date of Patent: *Nov. 17, 2020

(54) IONIC LIQUID COMPOSITION AND METHOD FOR DISSOLVING CELLULOSE USING THE SAME

(71) Applicant: Panasonic Intellectual Property Management Co., Ltd., Osaka (JP)

(72) Inventors: Takahiro Aoki, Osaka (JP); Tomoko Kawashima, Osaka (JP); Haruka Kusukame, Kyoto (JP); Yuko Taniike, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 265 days.

This patent is subject to a terminal disclaimer.

(21) Appl. No.: 15/869,224

(22) Filed: Jan. 12, 2018

(65) Prior Publication Data
US 2018/0215942 A1 Aug. 2, 2018

(30) Foreign Application Priority Data
Jan. 30, 2017 (JP) .................... 2017-013884

(51) Int. Cl.
*C09D 101/02* (2006.01)
*C08B 1/00* (2006.01)
(Continued)

(52) U.S. Cl.
CPC .......... *C09D 101/02* (2013.01); *B05D 3/107* (2013.01); *C07C 215/40* (2013.01);
(Continued)

(58) Field of Classification Search
CPC ........ C09D 101/02; C09D 7/20; B05D 3/107; C07C 215/40; C07C 229/26;
(Continued)

(56) References Cited

U.S. PATENT DOCUMENTS

| | | | | |
|---|---|---|---|---|
| 2011/0247494 | A1* | 10/2011 | Dinnage | B01D 53/1456 95/92 |
| 2015/0368371 | A1* | 12/2015 | Rogers | C08J 3/14 524/13 |
| 2016/0082141 | A1* | 3/2016 | Rogers | A61L 15/225 602/48 |

FOREIGN PATENT DOCUMENTS

| | | |
|---|---|---|
| JP | 2012-144441 | 8/2012 |
| JP | 2015-096255 | 5/2015 |
| JP | 2016-145272 | 8/2016 |

OTHER PUBLICATIONS

Ning Sun et al., "Understanding pretreatment efficacy of four cholinium and imidazolium ionic liquids by chemistry and computation", Royal Society of Chemistry, Green Chem., 2014, Jan. 30, 2014, pp. 2546-2557.

(Continued)

*Primary Examiner* — Robert S Walters, Jr.
(74) *Attorney, Agent, or Firm* — McDermott Will & Emery LLP

(57) ABSTRACT

The present invention provides an ionic liquid composition containing an ionic liquid and water. The ionic liquid composition does not contain an enzyme capable of hydrolyzing cellulose. The ionic liquid is represented by the following chemical formula (I): $[(CH_3)_3N(CH_2)_2OH]^+ [NH_2\text{-}L\text{-}CHNH_2\text{---}COO]^-$ (I); where L is absent or a linker. A molar ratio of $[(CH_3)_3N(CH_2)_2OH]^+$ to $[NH_2\text{-}L\text{-}CHNH_2\text{---}COO]^-$ is not less than 0.87 and not more than 1.14. A weight ratio of the water to the ionic liquid composition is not more than 7.3%. The present invention provides an ionic liquid composition capable of dissolving cellulose without a cellulose-degrading enzyme, namely, an enzyme capable of hydrolyzing cellulose.

28 Claims, 10 Drawing Sheets

(51) Int. Cl.
*C08J 5/00* (2006.01)
*B05D 3/10* (2006.01)
*C09D 7/20* (2018.01)
*C07C 229/26* (2006.01)
*C08J 3/09* (2006.01)
*C08L 1/02* (2006.01)
*C07C 231/00* (2006.01)
*C07C 215/40* (2006.01)

(52) U.S. Cl.
CPC .......... *C07C 229/26* (2013.01); *C07C 231/00* (2013.01); *C08B 1/003* (2013.01); *C08J 3/096* (2013.01); *C08J 5/00* (2013.01); *C08L 1/02* (2013.01); *C09D 7/20* (2018.01); *C08J 2301/02* (2013.01)

(58) Field of Classification Search
CPC ........ C07C 231/00; C08B 1/003; C08J 3/096; C08J 5/00; C08J 2301/02; C08L 1/02
See application file for complete search history.

(56) References Cited

OTHER PUBLICATIONS

Qiu-Ping Liu et al., "Ionic liquids from renewable biomaterials: synthesis, characterization and application in the pretreatment of biomass", Green Chem., 2012, 14, 304, Dec. 14, 2011, and Supplementary materials thereof.

\* cited by examiner

IONIC LIQUID COMPOSITION AND METHOD FOR DISSOLVING CELLULOSE USING THE SAME

BACKGROUND

1. Technical Field

The present invention relates to an ionic liquid composition and a method for dissolving cellulose using the same.

2. Description of the Related Art

Patent Literature 1 discloses using an ionic liquid as an enzyme saccharification pretreatment agent of cellulosic biomass. Patent Literature 1 discloses choline acetate as an ionic liquid in the paragraph [0037]. Furthermore, in the paragraph [0022], Patent Literature 1 discloses that an example of the anion of the ionic liquid is an amino acid anion such as glutaminic acid.

Patent Literature 2 discloses an ionic liquid, a purification method of the ionic liquid, and a treatment method of cellulose-based biomass. Patent Literature 2 discloses in the paragraphs [0024]-[0026] that an example of the anion of the ionic liquid is an amino acid anion such as alanine, lysine, threonine, isoleucine, asparagine, valine, phenylalanine, tyrosine, methionine, leucine, or ornithine.

Non Patent Literature 1 and Non Patent Literature 2 disclose degradation of cellulose using a cellulose-degrading enzyme (namely, enzyme capable of hydrolyzing cellulose) together with the degradation accelerator of an ionic liquid consisting of $[(CH_3)_3NCH_2CH_2OH]^+[NH_2(CH_2)_4CH(NH_2)COO]^-$ (hereinafter, referred to as "[Ch][Lys]").

CITATION LIST

Patent Literature 1
Japanese patent laid-open publication No. 2015-096255A
Patent Literature 2
Japanese patent laid-open publication No. 2012-144441A
Patent Literature 3
Japanese patent laid-open publication No. 2016-145272A
Non Patent Literature 1
Ning Sun et. al., "Understanding pretreatment efficacy of four cholinium and imidazolium ionic liquids by chemistry and computation", Royal Society of Chemistry, Green Chem., 2014, 16, 2546-2557
Non Patent Literature 2
Qiu-Ping Liu et. al., "Ionic liquids from renewable biomaterials: synthesis, characterization and application in the pretreatment of biomass", Green Chemistry, 2012, 14, 304-307

SUMMARY

The present invention provides an ionic liquid composition containing,
an ionic liquid; and
water,
wherein
the ionic liquid composition does not contain an enzyme capable of hydrolyzing cellulose;
the ionic liquid is represented by the following chemical formula (I):

      (I)

where
L is absent or a linker;
a molar ratio of $[(CH_3)_3N(CH_2)_2OH]^+$ to $[NH_2\text{-L-}CHNH_2\text{—COO}]^-$ is not less than 0.87 and not more than 1.14; and
a weight ratio of the water to the ionic liquid composition is not more than 7.3%.

The present invention also provides a method for dissolving cellulose using the above ionic liquid composition.

The present invention further also provides a method for fabricating a cellulose film using the above ionic liquid composition.

The present invention provides an ionic liquid composition capable of dissolving cellulose without a cellulose-degrading enzyme, namely, an enzyme capable of hydrolyzing cellulose.

DETAILED DESCRIPTION OF THE EMBODIMENT

Figure 1:
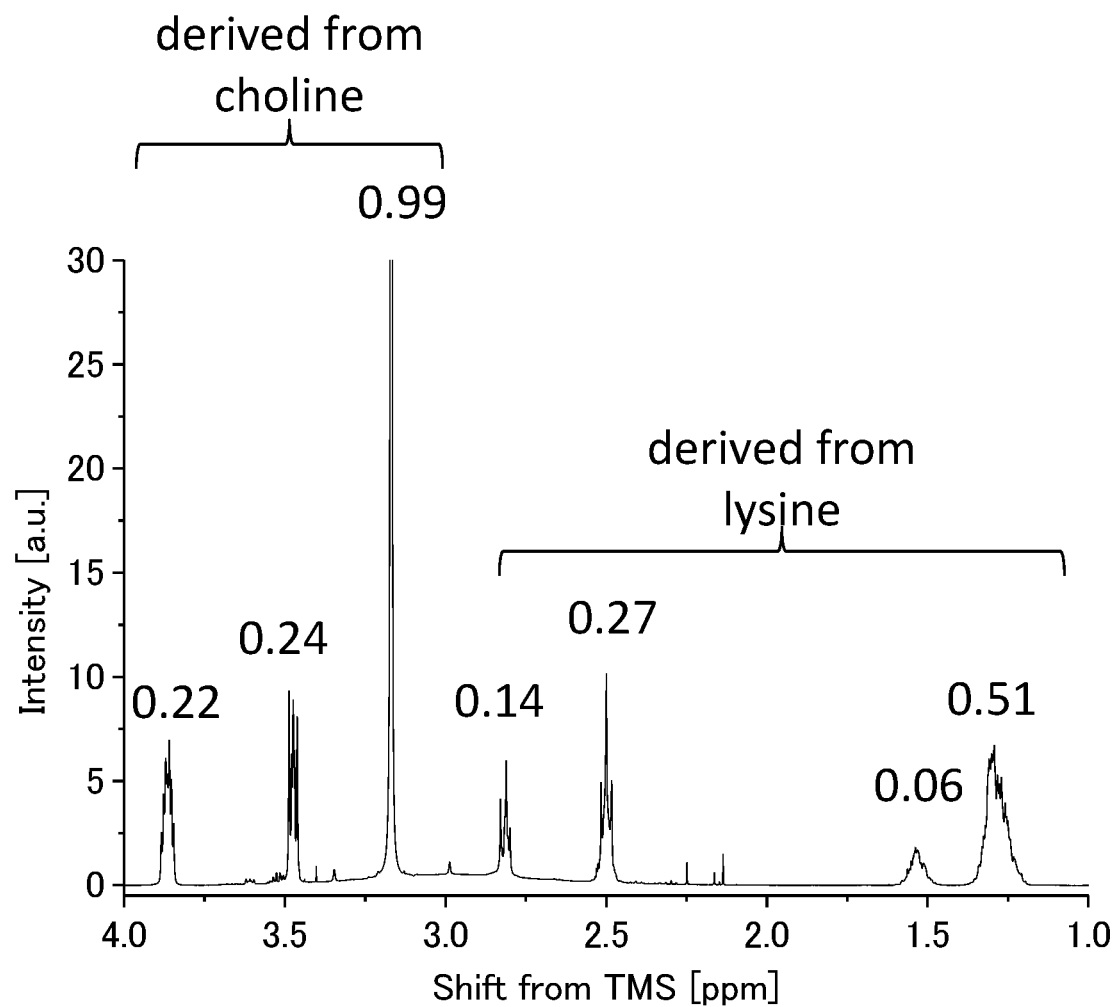
FIG. 1 shows a result of the nuclear magnetic resonance spectrum $^1$H-NMR measurement in the inventive example 1A.

Hereinafter, the embodiment of the present invention will be described.

The ionic liquid composition according to the present embodiment contains an ionic liquid and water. Unlike the disclosure of Non Patent Literature 1 and Non Patent Literature 2, the ionic liquid composition according to the present embodiment does not contain a cellulose-degrading enzyme, namely, an anzyme capable of hydrolyzing cellulose.

The ionic liquid is represented by the following chemical formula (I);

      (I)

where

L is absent or a linker.

A molar ratio of $[(CH_3)_3N(CH_2)_2OH]^+$ to $[NH_2\text{-L-}CHNH_2\text{—}COO]^-$ is not less than 0.87 and not more than 1.14. A weight ratio of the water to the ionic liquid composition is not more than 7.3%.

Cellulose is added to the ionic liquid composition according to the present embodiment. In this way, the cellulose is dissolved in the ionic liquid composition to provide a cellulose solution. Desirably, the cellulose has a weight average molecular weight of not less than 30,000. Desirably, the cellulose has a weight average molecular weight of not more than 500,000.

As well known, an ionic liquid is composed of a cation and an anion. In the present embodiment, the cation is a choline cation represented by the chemical formula $[(CH_3)_3N(CH_2)_2OH]^+$ (hereinafter, referred to as "[Ch]"). Choline is an aqueous nutrient essential for a human. In the present embodiment, the anion is represented by the chemical formula $[NH_2\text{-L-CHNH}_2\text{—}COO]^-$. Desirably, L is $\text{—}(CH_2)_n\text{—}$ (where n is a natural number). More desirably, n is equal to 3 or 4. In other words, the anion is an ornithine anion represented by the chemical formula $[NH_2\text{—}(CH_2)_3\text{—}CHNH_2\text{—}COO]^-$ or a lysine anion represented by the chemical formula $[NH_2\text{—}(CH_2)_4\text{—}CHNH_2\text{—}COO]^-$. Ornithine and lysine are each one kind of amino acids. For simple expression, choline cation, ornithine anion, and lysine anion may be represented by [Ch], [Orn], and [Lys] respectively in the present specification.

[Ch], [Orn], and [Lys] exist in a human body, and are materials having high safety for a living body for the reason of holding of matabolic pathway in a body and other reasons.

In addition, for the reason that hydrogen bonding strength of an amino group or a carboxyl group derived from ornithinate or lysinate is greater than hydrogen bonding strength of OH groups between cellulose chains and other reasons, the ionic liquid according to the present disclosure is capable of weaking hydrogen bonds between the cellulose chains and the effect of improving solubility of cellulose is expected.

The ionic liquid represented by the chemical formula [Ch][Orn] may be synthesized on the basis of the following chemical reaction formula (II). As shown in the following chemical reaction formula (II), choline is mixed with ornithine hydrochloride. The molar quantity of choline is twice as much as that of ornithine hydrochloride. The mixture solution containing choline and ornithine is heated under reduced pressure vacuume, and then dried to provide the ionic liquid represented by the chemical formula [Ch][Orn] through dehydration reaction between the hydroxyl ion of the choline and the hydrogen ion of the carboxyl group of the ornithine. However, the synthesis process is not limited to this process and does not matter if the [Ch][Orn] is synthesized finally.

[Chem. 1]

(II)

$2([(CH_3)_3N(CH_2)_2OH]^+[OH]^-)\ +$

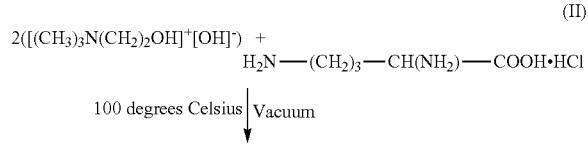

$[(CH_3)_3N(CH_2)_2OH]^+[H_2N\text{—}(CH_2)_3\text{—}CH(NH_2)\text{—}COO]^-$
$+$
$[(CH_3)_3N(CH_2)_2OH]^+[Cl]^-$
$+$
$H_2O$ The ionic liquid represented by the chemical formula [Ch][Lys] may be synthesized on the basis of the following chemical reaction formula (III). As shown in the following chemical reaction formula (III), choline is mixed with lysine. The molar quantity of choline is equal to the molar quantity of lysine. The mixture solution containing choline and lysine is heated under reduced pressure, and then dried to provide the ionic liquid represented by the chemical formula [Ch][Lys] through dehydration reaction between the hydroxyl ion of the choline and the hydrogen ion of the carboxyl group of the lysine. However, the synthesis process is not limited to this process and does not matter if the [Ch][Lys] is synthesized finally.

[Chem. 2]

(III)

$[(CH_3)_3N(CH_2)_2OH]^+[OH]^-)\ +$

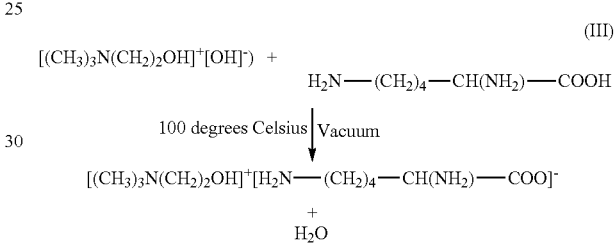

In the present embodiment, the molar ratio of $[(CH_3)_3N(CH_2)_2OH]^+$ to $[NH_2\text{-L-CHNH}_2\text{—}COO]^-$ is not less than 0.87 and not more than 1.14. As is clear from the inventive examples and the comparative examples which will be described later, in case where the molar ratio is less than 0.87, cellulose fails to be dissolved in the ionic liquid composition within forty-eight hours. Also in case where the molar ratio is more than 1.14, cellulose fails to be dissolved in the ionic liquid composition within forty-eight hours.

A weight ratio of the water to the ionic liquid composition is not more than 7.3%. As is clear from the inventive examples and the comparative examples which will be described later, in case the weight ratio is more than 7.3%, cellulose fails to be dissolved in the ionic liquid composition within forty-eight hours. Time necessary for dissolving cellulose is also decreased with a decrease in the weight ratio. Therefore, it is desirable that the weight ratio is small. As one example, the lower limit of the weight ratio is 1.3%. However, as is clear from the above chemical reaction formula (II) and chemical reaction formula (III), note that water is generated as by-product upon the synthesis of the ionic liquid.

As one embodiment, the ionic liquid composition according to the present embodiment dissolves cellulose within forty-eight hours, desirably, within twenty-four hours, after the cellulose is added to the ionic liquid composition according to the present embodiment. Unlike the disclosure of Non Patent Literature 1 and Non Patent Literature 2, a cellulose-degrading enzyme is not used in this embodiment. As is disclosed in Patent Literature 3, a cellulose sheet is formed from the ionic liquid composition to which the cellulose has been added, namely, from the cellulose solution.

It is desirable that the ionic liquid composition to which the cellulose has been added is heated in order to promote the dissolution. As one embodiment, the ionic liquid composition to which the cellulose has been added is heated at a temperature of not less than 70 degrees Celsius and not more than 100 degrees Celsius at a pressure of not less than 0.01 MPa and not more than 0.1 MPa for not less than twenty four hours.

The ionic liquid composition to which the cellulose has been added may be left at rest until the cellulose is dissolved in the ionic liquid composition. The ionic liquid composition to which the cellulose has been added may be stirred.

A kind of the cellulose dissoluble in the ionic liquid of the present disclosure is not limited particularly. For example, native cellulose derived from plant species or artificial cellulose such as cellophane or manufactured cellulose such as cellulose nanofiber may be applied. In addition, it does not depend on the crystalline state of original cellulose. In other words, it is known that cellulose has an I-type-IV-type crystalline structure or a non-crystalline structure. Cellulose having any structure may be dissolved.

The ionic liquid composition according to the present embodiment may contain other components. An example of the other components is an aprotic polar solvent. The ionic liquid composition according to the present embodiment is in a liquid state.

As described above, the ionic liquid composition according to the present embodiment may contain an aprotic polar solvent in order to control a viscosity thereof. An example of the aprotic polar solvent is dimethyl sulfoxide. The weight ratio of the ionic liquid to the aprotic polar solvent may be not less than 309% in the ionic liquid composition.

Unlike the disclosure of Non Patent Literature 1 and Non Patent Literature 2, the ionic liquid composition according to the present embodiment does not contain cellulose-degrading enzyme.

EXAMPLES

Hereinafter, the present invention will be described in more detail with reference to the following examples.

(Experiment 1)

The experiment 1 is composed of inventive examples 1A-1J and comparative examples 1A-1E. In the experiment 1, the cation was choline and the anion was lysine.

Inventive Example 1A

L-lysine (available from Tokyo Chemical Industry Co., Ltd., 14.6 grams, 100 millimoles) was mixed with a choline aqueous solution (available from Tokyo Chemical Industry Co., Ltd., 24.7 grams, 100 millimoles) to provide a mixture solution. The mixture solution was dried at a temperature of 100 degrees Celsius under reduced pressure for three hours. In this way, an ionic liquid composition containing an ionic liquid represented by the chemical formula [Ch][Lys] was provided.

The thus-provided [Ch][Lys] ionic liquid composition was confirmed by using nuclear magnetic resonance spectrum measurement. Please note that the structure of the ionic liquid composition fabricated in the present example were determined with nuclear magnetic resonance spectrum (measured with Unity (nova-400 made by Varian company, 400 MHz; $^1$H-NMR). The measurement was conducted using deuterated DMSO and indicated with δ value (ppm) when tetramethyl silane (i.e., TMS) was an internal standard. FIG. 1 shows a result of the nuclear magnetic resonance spectrum $^1$H-NMR measurement in the inventive example 1A.

In addition, a water amount contained in the [Ch][Lys] ionic liquid composition (500 milligrams) was measured by Karl Fischer's method. In this method, the weight of the [Ch][Lys] ionic liquid composition was measured three times to calculate the average weight thereof, and then this ionic liquid composition was injected to a moisture measurement device CA-100 (available from Mitsubishi Chemical Analytech Co., Ltd.). The weight of the residual moisture was measured and a water ratio was calculated by dividing by the weight of the ionic liquid composition. As a result, the water amount of the [Ch][Lys] ionic liquid composition was 1.3% (6.3 milligrams).

The [Ch][Lys] ionic liquid composition having a weight of 0.97 grams was supplied to a glass bottle. Cellulose (0.03 grams, available from Sigma-Aldrich, trade name: Avicel PH-101, average molecular weight measured by a gel-permeation chromatography-multi angle light scattering method: approximately 30,000) was added to the glass bottle. The solution was stored at a temperature of 90 degrees Celsius at a pressure of 0.02 MPa. The present inventors observed visually whether or not the added cellulose was dissolved in the [Ch][Lys] ionic liquid composition. As a result, after five hours elapsed from the mixture of the ionic liquid composition and the cellulose, the cellulose was dissolved in the [Ch][Lys] ionic liquid composition. Furthermore, on the basis that the peak derived from the crystalline property of the cellulose disappeared in the X-ray diffraction analysis result, the present inventors confirmed the dissolution of the cellulose.

The ratio of the cation [Ch] to the anion [Lys] in the provided [Ch][Lys] ionic liquid composition was measured as below. In the $^1$H-NMR spectrum shown in FIG. 1, three peaks each having a shift value of not less than 3.0 are derived from choline. The values of area ratio of the three peaks are 0.22, 0.24, and 0.99. A choline molecular has fourteen hydrogen atoms. However, one hydroxyl group included in the choline molecular does not appear in the $^1$H-NMR. Therefore, in FIG. 1, the thirteen hydrogen atoms included in the choline molecular appear. On the other hand, four peaks each having a shift value of less than 3.0 are derived from lysine. The values of area ratio of the four peaks are 0.14, 0.27, 0.06, and 0.51. A lysine molecule has thirteen hydrogen atoms. However, four hydrogen atoms included in two amino acid groups included in the lysine molecule do not appear in the $^1$H-NMR. Therefore, in FIG. 1, nine hydrogen atoms included in the lysine molecular appears.

As is well known, the area of $^1$H-NMR is proportional to the number of the hydrogen atoms. Therefore, the ratio of the [Ch] cation to the [Lys] anion included in the [Ch][Lys] ionic liquid composition is calculated on the basis of the following mathematical formula (X). Hereinafter, the ratio is referred to as "RCA".

RCA=(the sum total of the area ratio of the peaks derived from the cation/the number of the hydrogen atoms which is included in the cation and appears in the $^1$H-NMR)/(the sum total of the area ratio of the peaks derived from the anion/the number of the hydrogen atoms which is included in the anion and appears in the $^1$H-NMR)    (X)

In the inventive example 1 (namely, in FIG. 1), the sum total of the area ratio of the peaks derived from the cation, namely, choline=0.22+0.24+0.99=1.45 the number of the hydrogen atoms which is included in the cation (namely, choline) and appears in the $^1$H-NMR=13 the sum total of the area ratio of the peaks derived from the anion, namely, lysine=0.14+0.27+0.06+0.51=0.98 the number of the hydrogen atoms which is included in the anion (namely, lysine) and appears in the $^1$H-NMR=9

Therefore, the value of RCA is calculated to be approximately 1.02, as shown in the following mathematical formula.

$$RCA=(1.45/13)/(0.98/9)=\text{approximately } 1.02$$

Inventive Example 1B

Figure 2:
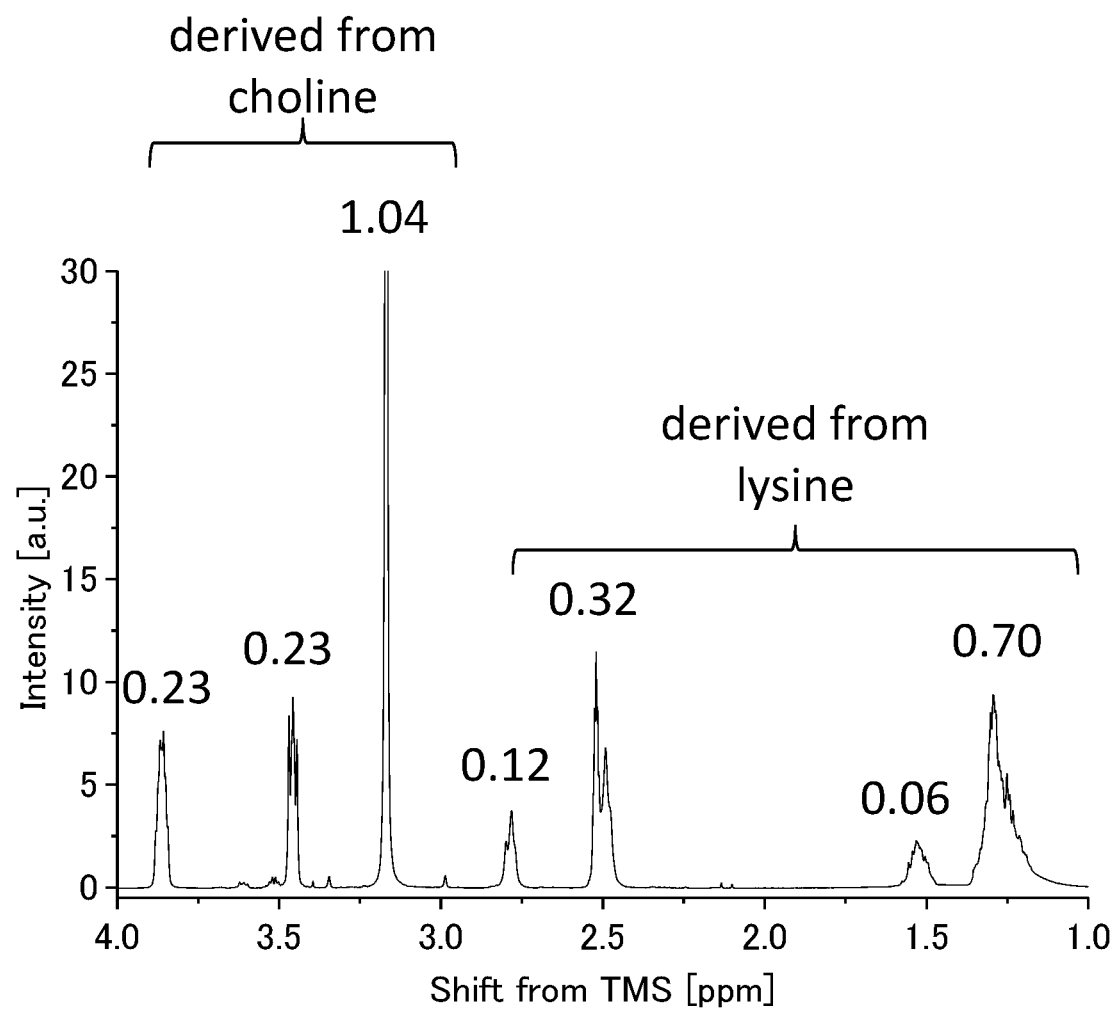
FIG. 2 shows a result of the nuclear magnetic resonance spectrum $^1$H-NMR measurement in the inventive example 1B.

In the inventive example 1B, an experiment similar to the inventive example 1A was conducted, except that the weight of the lysine was 16.8 grams (approximately, 0.115 moles). FIG. 2 shows a result of the nuclear magnetic resonance spectrum $^1$H-NMR measurement in the inventive example 1B. The value of RCA calculated on the basis of FIG. 2 was 0.87. In the inventive example 1B, the cellulose was dissolved.

Inventive Example 1C

Figure 3:
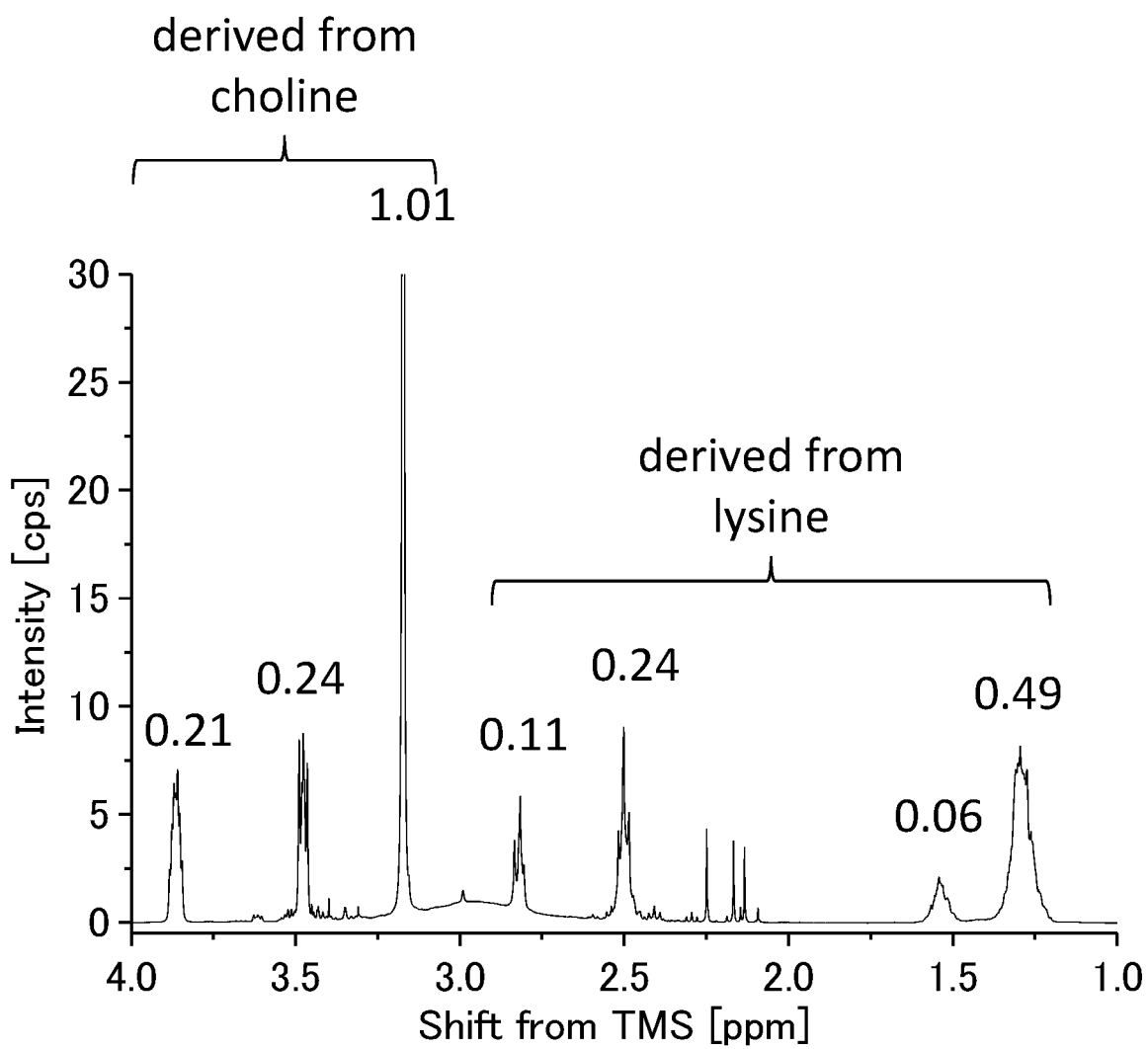
FIG. 3 shows a result of the nuclear magnetic resonance spectrum $^1$H-NMR measurement in the inventive example 1C.

In the inventive example 1C, an experiment similar to the inventive example 1A was conducted, except that the weight of the lysine was 13.0 grams (approximately, 0.089 moles). FIG. 3 shows a result of the nuclear magnetic resonance spectrum $^1$H-NMR measurement in the inventive example 1C. The value of RCA calculated on the basis of FIG. 3 was 1.12. In the inventive example 1C, the cellulose was dissolved.

Inventive Example 1D

In the inventive example 1D, an experiment similar to the inventive example 1A was conducted, except of using bleached pulp made from wood (average molecular weight: approximately 300,000-500,000) in place of the cellulose Avicel PH-101. In the inventive example 1D, the cellulose was dissolved after twenty-four hours elapsed from the mixture of the ionic liquid composition and the cellulose (i.e., bleached pulp).

Inventive Example 1E

In the inventive example 1E, an experiment similar to the inventive example 1A was conducted, except that the ionic liquid composition (0.97 grams) according to the inventive example 1A further contained water (0.029 grams, 4.3 weight percent) and except of using bleached pulp made from wood (average molecular weight: approximately 300,000-500,000) in place of the cellulose Avicel PH-101. In the inventive example 1E, the cellulose was dissolved after twenty-four hours elapsed from the mixture of the ionic liquid composition and the cellulose (i.e., bleached pulp).

Inventive Example 1F

In the inventive example 1F, an experiment similar to the inventive example 1A was conducted, except that the ionic liquid composition (0.97 grams) according to the inventive example 1A further contained water (0.049 grams, 6.3 weight percent) and except of using bleached pulp made from wood (average molecular weight: approximately 300,000-500,000) in place of the cellulose Avicel PH-101. In the inventive example 1F, the cellulose was dissolved after thirty-two hours elapsed from the mixture of the ionic liquid composition and the cellulose (i.e., bleached pulp).

Inventive Example 1G

In the inventive example 1G, an experiment similar to the inventive example 1A was conducted, except that the ionic liquid composition (0.97 grams) according to the inventive example 1A further contained water (0.058 grams, 7.3 weight percent) and except of using bleached pulp made from wood (average molecular weight: approximately 300,000-500,000) in place of the cellulose Avicel PH-101. In the inventive example 1G, the cellulose was dissolved after forty-one hours elapsed from the mixture of the ionic liquid composition and the cellulose (i.e., bleached pulp).

Comparative Example 1A

Figure 4:
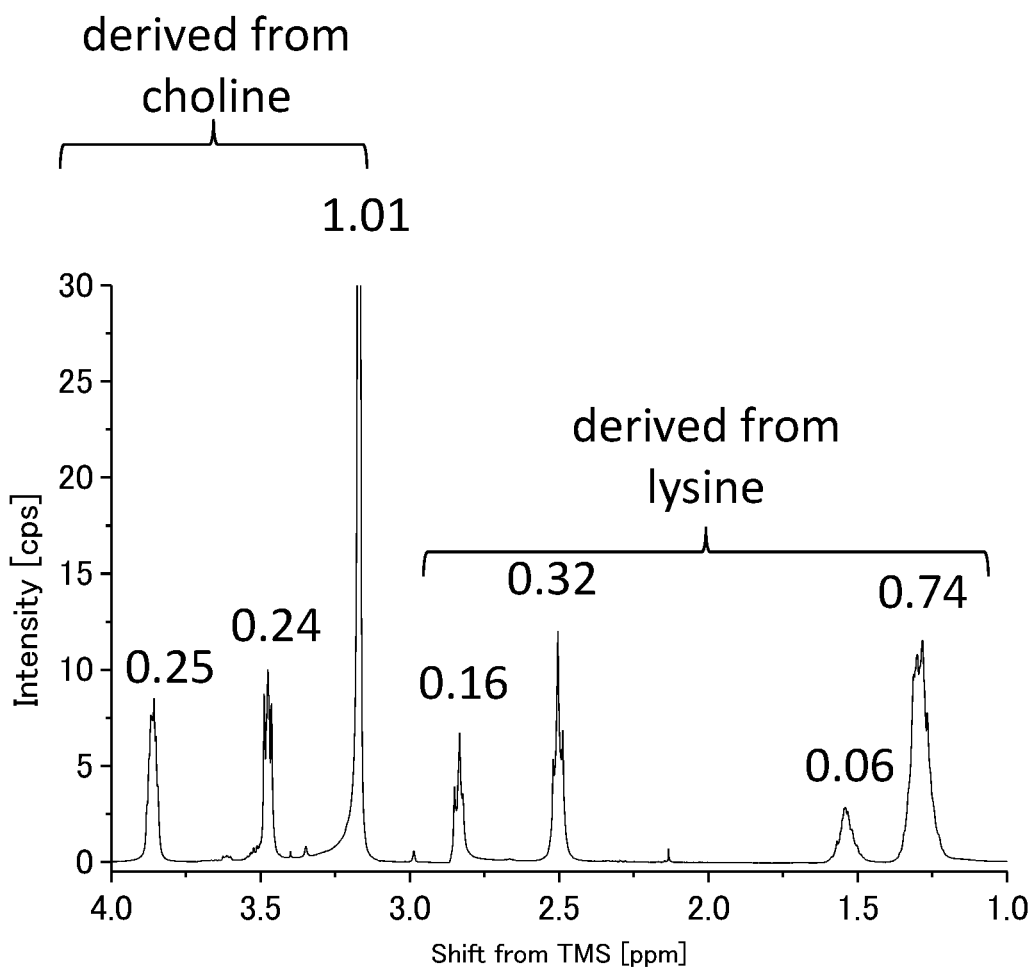
FIG. 4 shows a result of the nuclear magnetic resonance spectrum $^1$H-NMR measurement in the comparative example 1A.

In the comparative example 1A, an experiment similar to the inventive example 1A was conducted, except that the weight of the lysine was 18.0 grams (approximately, 0.123 moles). FIG. 4 shows a result of the nuclear magnetic resonance spectrum $^1$H-NMR measurement in the comparative example 1A. The value of RCA calculated on the basis of FIG. 4 was 0.81. In the comparative example 1A, the cellulose was not dissolved.

Comparative Example 1B

Figure 5:
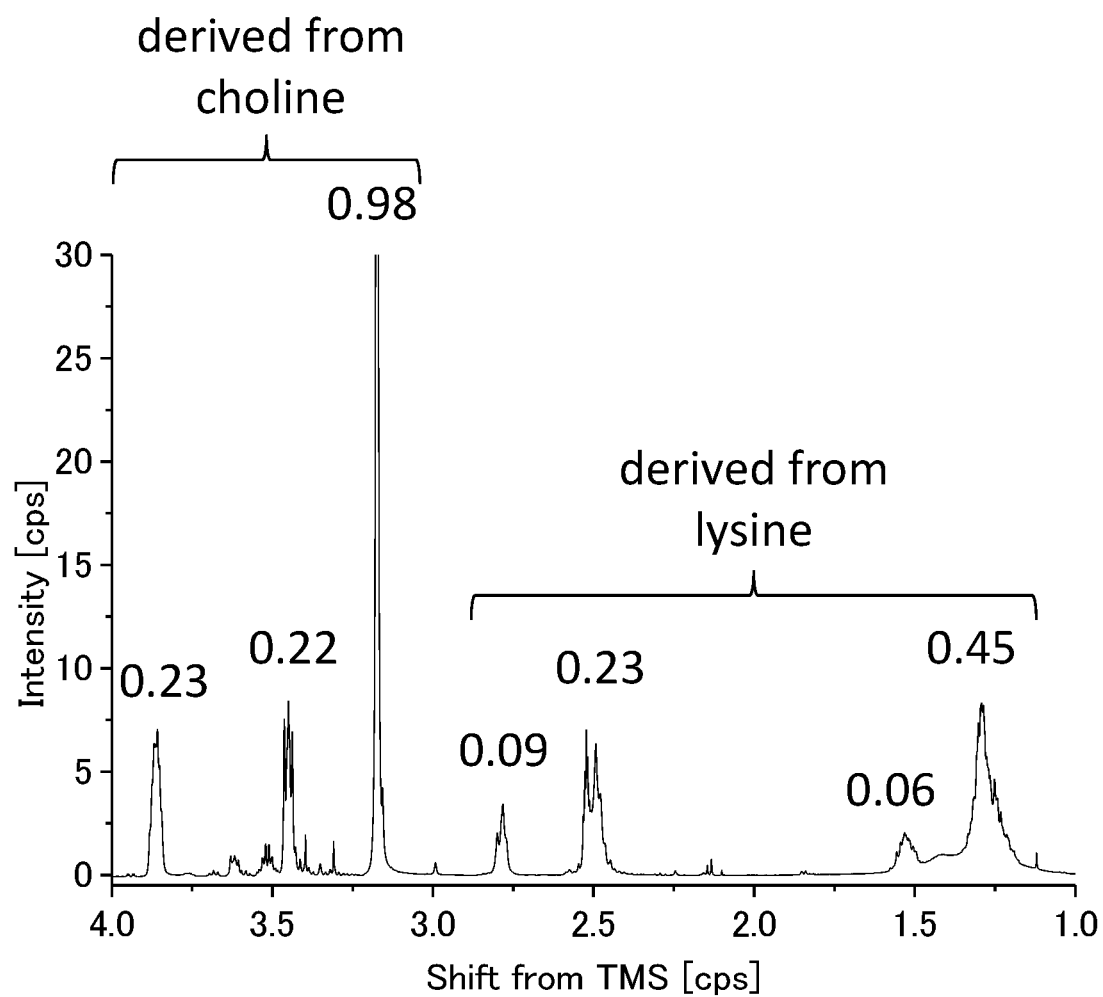
FIG. 5 shows a result of the nuclear magnetic resonance spectrum $^1$H-NMR measurement in the comparative example 1B.

In the comparative example 1B, an experiment similar to the inventive example 1A was conducted, except that the weight of the lysine was 12.3 grams (approximately, 0.084 moles). FIG. 5 shows a result of the nuclear magnetic resonance spectrum $^1$H-NMR measurement in the comparative example 1B. The value of RCA calculated on the basis of FIG. 5 was 1.19. In the comparative example 1B, the cellulose was not dissolved, even after one hundred hours elapsed from the mixture of the ionic liquid composition and the cellulose.

Comparative Example 1C

In the comparative example 1C, an experiment similar to the inventive example 1A was conducted, except that the ionic liquid composition (0.97 grams) according to the inventive example 1A further contained water (0.068 grams, 8.3 weight percent) and except of using bleached pulp made from wood (average molecular weight: approximately 300,000-500,000) in place of the cellulose Avicel PH-101. In the comparative example 1C, the cellulose was not dissolved, even after one hundred hours elapsed from the mixture of the ionic liquid composition and the cellulose (i.e., bleached pulp).

Comparative Example 1D

In the comparative example 1D, an experiment disclosed in Non Patent Literature 2 was conducted. In particular, lysine (17.5 grams, 120 millimoles) was added to a choline aqueous solution (available from Tokyo Chemical Industry Co., Ltd., 24.7 grams, 100 millimoles), while it was cooled. The lysine was dissolved in the choline aqueous solution. In this way, a mixture was provided.

Subsequently, water was removed from the mixture at a temperature of 55 degrees Celsius under reduced pressure for five hours. To the mixture, a mixture solution (1 liter) of acetonitrile (available from Wako Pure Chemical Industries, Ltd., 900 milliliters) and methanol (available from Wako Pure Chemical Industries, Ltd., 100 milliliters) was added. The eluted lysine was removed by filtration. Then, the acetonitrile and the methanol were removed at a temperature of 40 degrees Celsius under reduced pressure for five hours.

Furthermore, the mixture was dried at a temperature of 70 degrees Celsius under reduced pressure for forty-eight hours. In this way, an ionic liquid composition containing choline and lysine was provided. The ionic liquid composition containing choline and lysine is referred to as "[Ch][Lys] ionic liquid composition".

The water amount contained in the [Ch][Lys] ionic liquid composition (500 milligrams) was measured by Karl Fischer's method similarly to the case of the inventive example 1A. As a result, the [Ch][Lys] ionic liquid composition according to the comparative example 1D had a water amount of 10.2%.

Then, a bleached pulp made from wood (average molecular weight: approximately 300,000-500,000) was added to the [Ch][Lys] ionic liquid composition according to the comparative example 1D, similarly to the case of the inventive example 1D. In the comparative example 1D, the cellulose was not dissolved, even after one hundred hours elapsed from the mixture of the ionic liquid composition and the cellulose (i.e., bleached pulp).

The following Table 1 shows the results of the above inventive example 1A-the comparative example 1D.

TABLE 1

(Composition: [Ch][Lys])

| | The value of RCA | Water Amount | Results |
|---|---|---|---|
| Comparative example 1A | 0.81 | 1.6% | Not dissolved even after 100 hours elapsed from the mixture |
| Inventive example 1B | 0.87 | 1.7% | Dissolved after 5 hours elapsed from mixture |
| Inventive example 1A | 1.02 | 1.3% | Dissolved after 5 hours elapsed from mixture |
| Inventive example 1C | 1.12 | 1.5% | Dissolved after 5 hours elapsed from mixture |
| Comparative example 1B | 1.19 | 1.6% | Not dissolved even after 100 hours elapsed from the mixture |
| Inventive example 1D | 1.02 | 1.3% | Dissolved after 24 hours elapsed from mixture |
| Inventive example 1E | 1.02 | 4.3% | Dissolved after 24 hours elapsed from mixture |
| Inventive example 1F | 1.02 | 6.3% | Dissolved after 32 hours elapsed from mixture |
| Inventive example 1G | 1.02 | 7.3% | Dissolved after 41 hours elapsed from mixture |
| Comparative example 1C | 1.02 | 8.3% | Not dissolved even after 100 hours elapsed from the mixture |
| Comparative example 1D | 1.02 | 10.2% | Not dissolved even after 100 hours elapsed from the mixture |

The value of RCA: molar ratio of [Ch]/[Lys]
Water Amount: the value calculated in accordance with Karl Fischer's method, and defined according to water weight/ionic liquid composition weight As is clear from Table 1, if the value of RCA is not less than approximately 0.87 and not more than 1.12, the cellulose was dissolved in the ionic liquid composition within 48 hours after the mixture of the ionic liquid composition and the cellulose. On the other hand, if the value of RCA is not more than approximately 0.81 or not less than 1.19, the cellulose is not dissolved in the ionic liquid composition even after 48 hours.

Furthermore, if the water amount is not more than 7.3%, the cellulose was dissolved in the ionic liquid composition within 48 hours after the mixture of the ionic liquid composition and the cellulose. On the other hand, if the water amount is not less than 8.3%, the cellulose was not dissolved in the ionic liquid composition even after 100 hours.

It is obvious that a cellulose-degrading enzyme was not used in this experiment.

Inventive Example 1H

In the inventive example 1H, dimethyl sulfoxide (hereinafter, referred to as "DMSO", 1.00 gram, the weight ratio thereof to the ionic liquid [Ch][Lys]: 103%) was added to the cellulose solution (1.00 gram) provided in the example 1A. Then, this solution was left at rest at a temperature of 90 degrees Celsius at normal pressures for 48 hours. The present inventors visually observed whether or not the cellulose and the DMSO were dissolved in each other.

Inventive Example 1I

In the inventive example 1I, an experiment similar to the inventive example 1H was conducted, except of addition of 2.00 grams of DMSO (the weight ratio thereof to the ionic liquid [Ch][Lys]: 206%)

Inventive Example 1J

In the inventive example 1J, an experiment similar to the inventive example 1H was conducted, except of addition of 3.00 grams of DMSO (the weight ratio thereof to the ionic liquid [Ch][Lys]: 309%)

Comparative Example 1E

In the comparative example 1E, an experiment similar to the inventive example 1H was conducted, except of addition of 4.00 grams of DMSO (the weight ratio thereof to the ionic liquid [Ch][Lys]: 412%)

The following Table 2 shows the results of the above inventive example 1H-the comparative example 1E.

TABLE 2

| | Weight ratio of DMSO to [Ch][Lys] [%] | Result |
|---|---|---|
| Inventive Example 1H | 103 | Dissolved in each other |
| Inventive Example 1I | 206 | Dissolved in each other |
| Inventive Example 1J | 309 | Dissolved in each other |
| Comparative example 1E | 412 | Cellulose was precipitated |

As is clear from Table 2, if the weight ratio of the DMSO to the ionic liquid represented by [Ch][Lys] is not more than 309%, the DMSO and the ionic liquid were dissolved in each other within 48 hours. On the other hand, if the weight ratio of the DMSO is not less than 412%, the cellulose was precipitated within 48 hours.

Experiment 2

The experiment 2 is composed of inventive examples 2A-2J and comparative examples 2A-2E. In the experiment 2, the cation was choline and the anion was ornithine.

Inventive Example 2A

L-ornithine hydrochloride (available from Wako Pure Chemical Industries, Ltd., 8.4 grams, 50 millimoles) was mixed with a choline aqueous solution (available from Tokyo Chemical Industry Co., Ltd., 24.7 grams, 100 millimoles) to provide a mixture solution. The mixture solution was dried at a temperature of 100 degrees Celsius under reduced pressure for three hours. In this way, an ionic liquid composition containing [Ch][Orn] ionic liquid was provided. The weight of the provided ionic liquid composition was 15.3 grams. The yield was 85%. The by-product was choline chloride. Similarly to the case of the inventive example 1A, the provided [Ch][Orn] ionic liquid composition was confirmed by using nuclear magnetic resonance spectrum measurement. The water amount of the [Ch][Orn] ionic liquid composition was 1.3% (0.66 grams).

Figure 6:
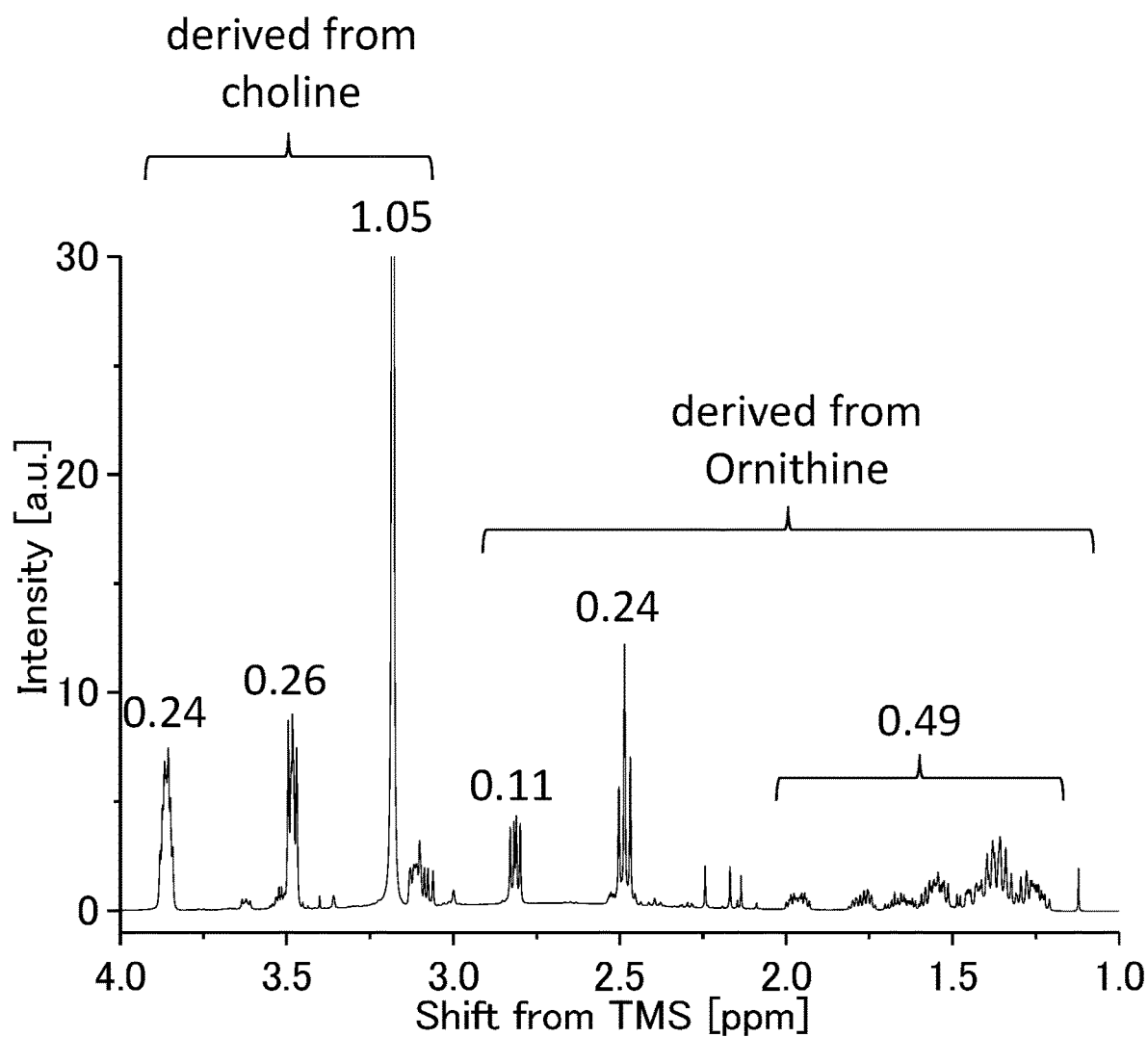
FIG. 6 shows a result of the nuclear magnetic resonance spectrum $^1$H-NMR measurement in the inventive example 2A.

FIG. 6 shows a result of the nuclear magnetic resonance spectrum $^1$H-NMR measurement in the inventive example 2A. The value of RCA calculated on the basis of FIG. 6 was 0.99. In the inventive example 2A, the cellulose was dissolved. Furthermore, as a basis that the peak derived from the crystalline property of the cellulose disappeared in the X-ray diffraction analysis result, the present inventors confirmed the dissolution of the cellulose.

Inventive Example 2B

Figure 7:
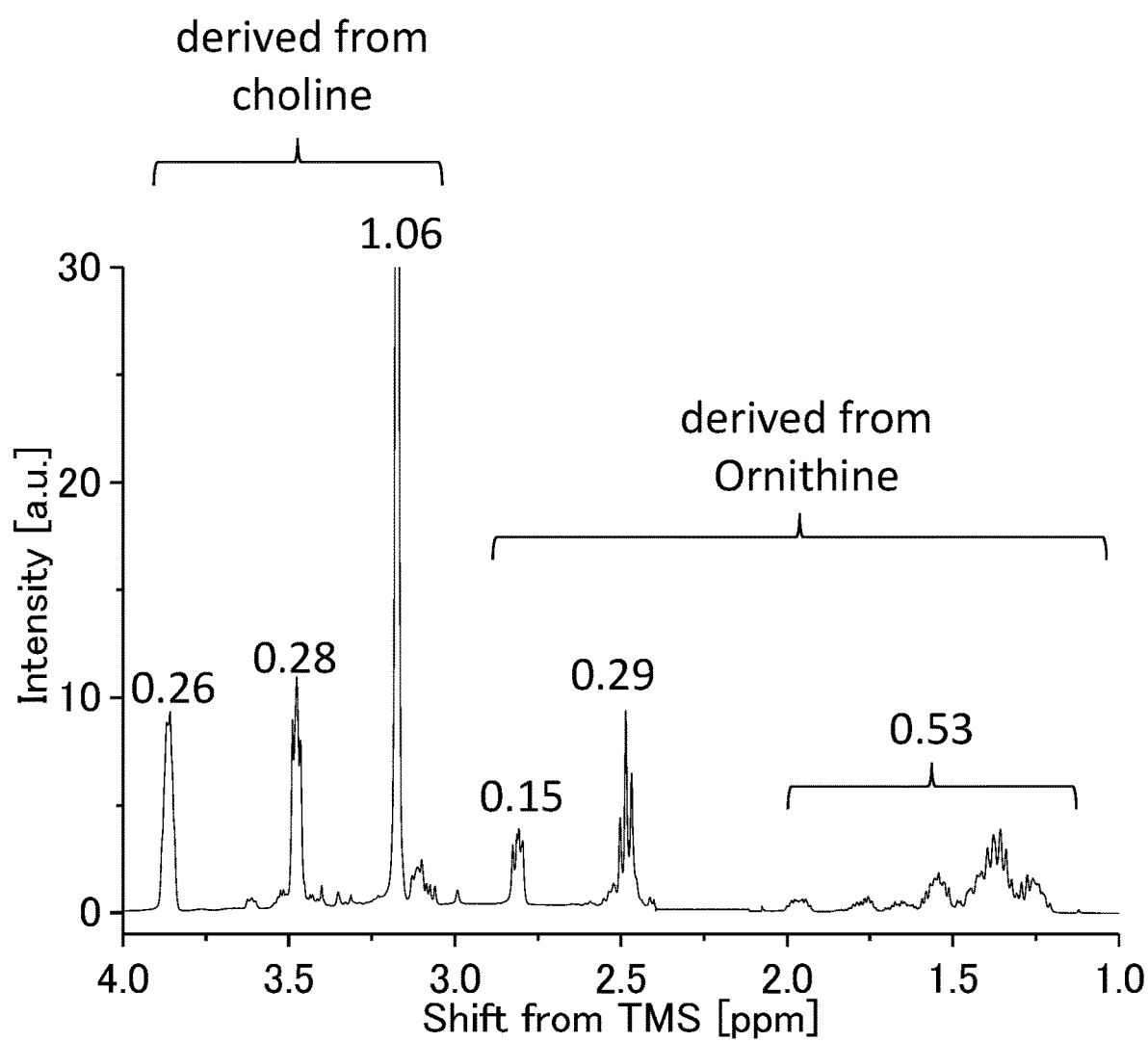
FIG. 7 shows a result of the nuclear magnetic resonance spectrum $^1$H-NMR measurement in the inventive example 2B.

In the inventive example 2B, an experiment similar to the inventive example 2A was conducted, except that the weight of the ornithine was 9.4 grams (approximately, 56 millimoles). FIG. 7 shows a result of the nuclear magnetic resonance spectrum $^1$H-NMR measurement in the inventive example 2B. The value of RCA calculated on the basis of FIG. 7 was 0.89. In the inventive example 2B, the cellulose was dissolved.

Inventive Example 2C

Figure 8:
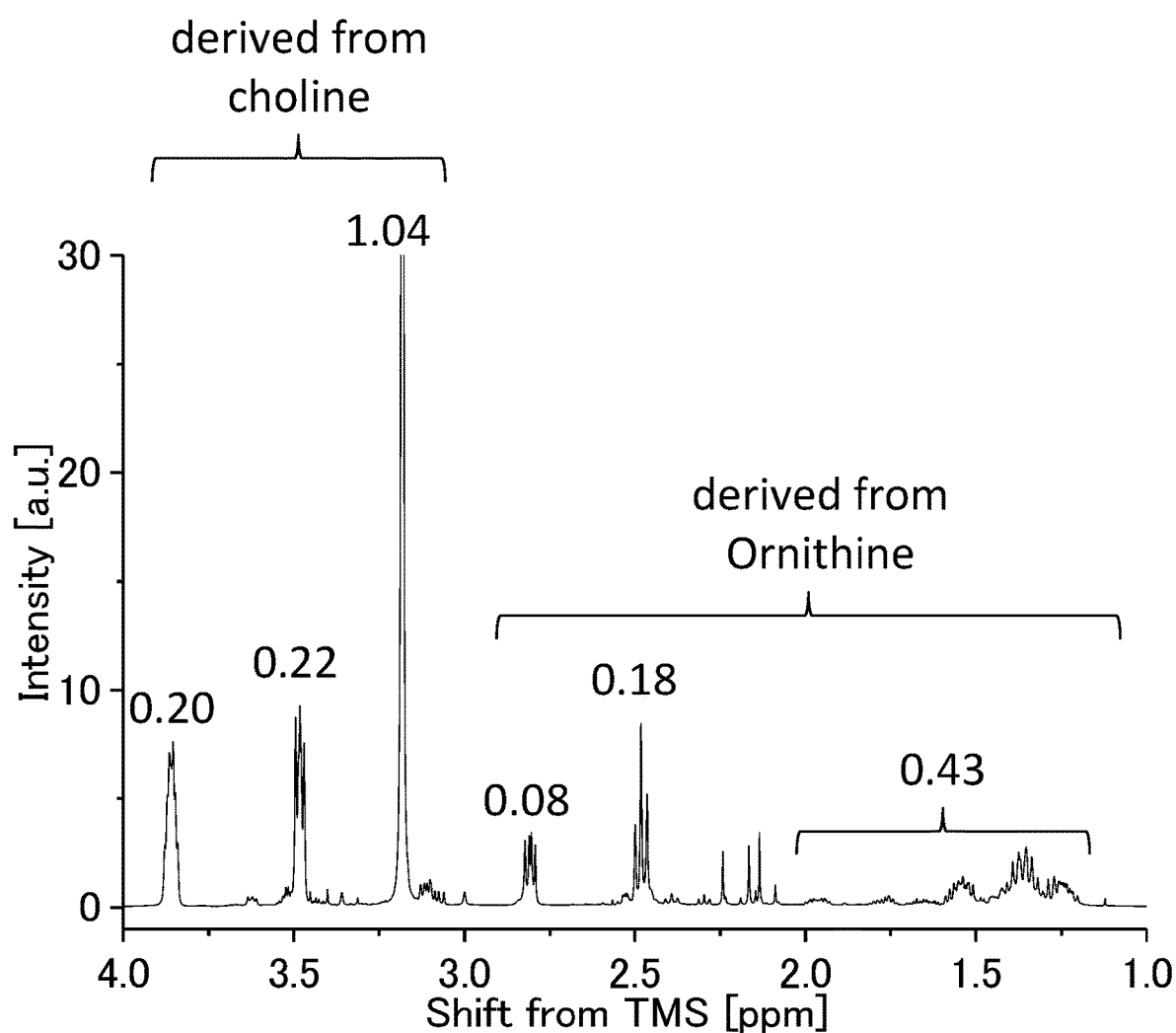
FIG. 8 shows a result of the nuclear magnetic resonance spectrum $^1$H-NMR measurement in the inventive example 2C.

In the inventive example 2C, an experiment similar to the inventive example 2A was conducted, except that the weight of the ornithine was 7.4 grams (approximately, 44 millimoles). FIG. 8 shows a result of the nuclear magnetic resonance spectrum $^1$H-NMR measurement in the inventive example 2C. The value of RCA calculated on the basis of FIG. 8 was 1.14. In the inventive example 2C, the cellulose was dissolved.

Inventive Example 2D

In the inventive example 2D, an experiment similar to the inventive example 2A was conducted, except of using bleached pulp made from wood (average molecular weight: approximately 300,000-500,000) in place of the cellulose Avicel PH-101. In the inventive example 2D, the cellulose was dissolved after twenty hours elapsed from the mixture of the ionic liquid composition and the cellulose (i.e., bleached pulp).

Inventive Example 2E

In the inventive example 2E, an experiment similar to the inventive example 2A was conducted, except that the ionic liquid composition (0.97 grams) according to the inventive example 2A further contained water (0.029 grams, 4.3 weight percent) and except of using bleached pulp made from wood (average molecular weight: approximately 300,000-500,000) in place of the cellulose Avicel PH-101. In the inventive example 2E, the cellulose was dissolved after twenty hours elapsed from the mixture of the ionic liquid composition and the cellulose (i.e., bleached pulp).

Inventive Example 2F

In the inventive example 2F, an experiment similar to the inventive example 2A was conducted, except that the ionic liquid composition (0.97 grams) according to the inventive example 2A further contained water (0.049 grams, 6.3 weight percent) and except of using bleached pulp made from wood (average molecular weight: approximately 300,000-500,000) in place of the cellulose Avicel PH-101. In the inventive example 2F, the cellulose was dissolved after thirty hours elapsed from the mixture of the ionic liquid composition and the cellulose (i.e., bleached pulp).

Inventive Example 2G

In the inventive example 2G, an experiment similar to the inventive example 2A was conducted, except that the ionic liquid composition (0.97 grams) according to the inventive example 2A further contained water (0.058 grams, 7.3 weight percent) and except of using bleached pulp made from wood (average molecular weight: approximately 300,000-500,000) in place of the cellulose Avicel PH-101. In the inventive example 2G, the cellulose was dissolved after forty hours elapsed from the mixture of the ionic liquid composition and the cellulose (i.e., bleached pulp).

Comparative Example 2A

Figure 9:
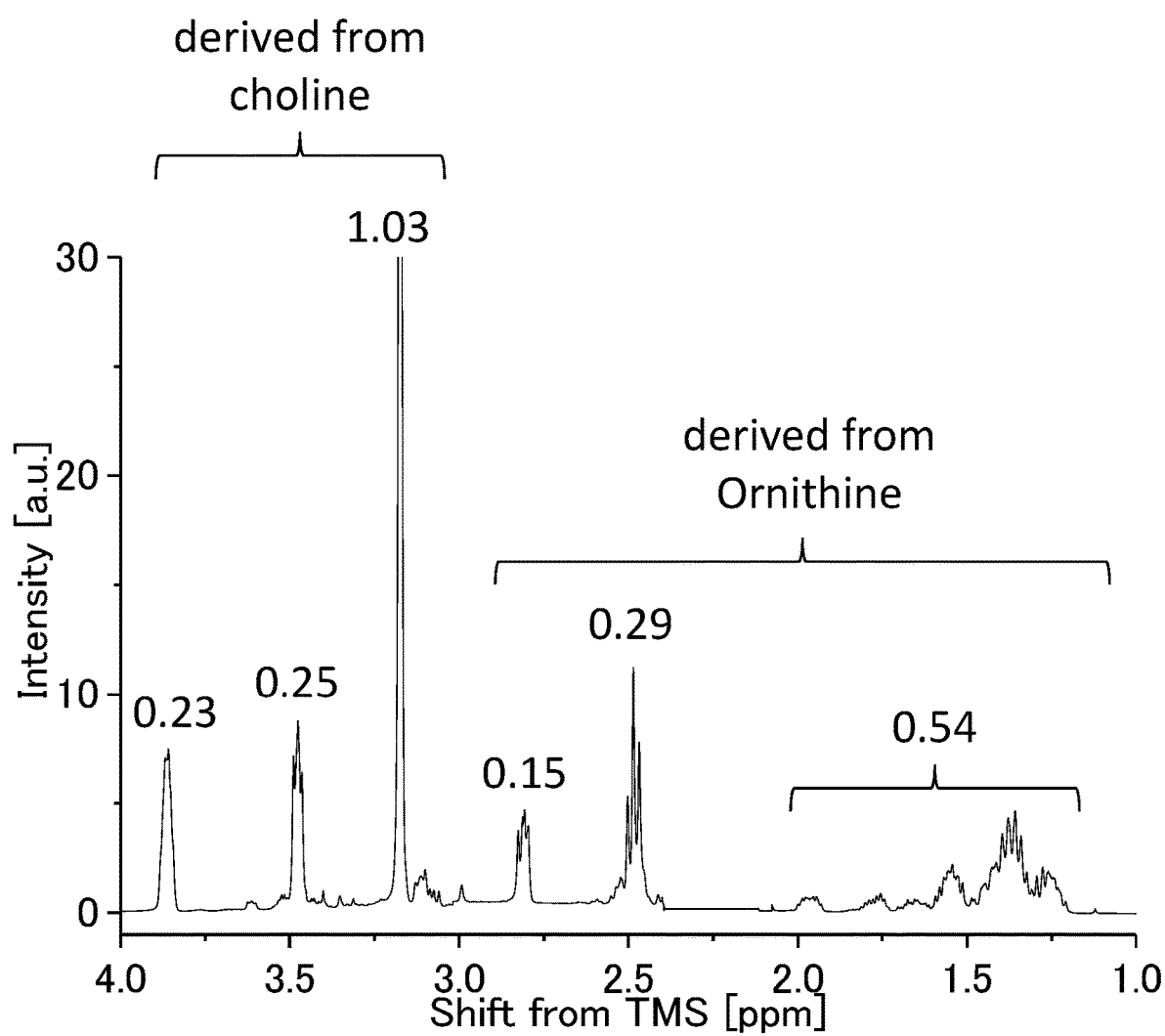
FIG. 9 shows a result of the nuclear magnetic resonance spectrum $^1$H-NMR measurement in the comparative example 2A.

In the comparative example 2A, an experiment similar to the inventive example 2A was conducted, except that the weight of the ornithine was 10.4 grams (approximately, 62 millimoles). FIG. 9 shows a result of the nuclear magnetic resonance spectrum $^1$H-NMR measurement in the comparative example 2A. The value of RCA calculated on the basis of FIG. 9 was 0.81. In the comparative example 2A, the cellulose was not dissolved.

Comparative Example 2B

Figure 10:
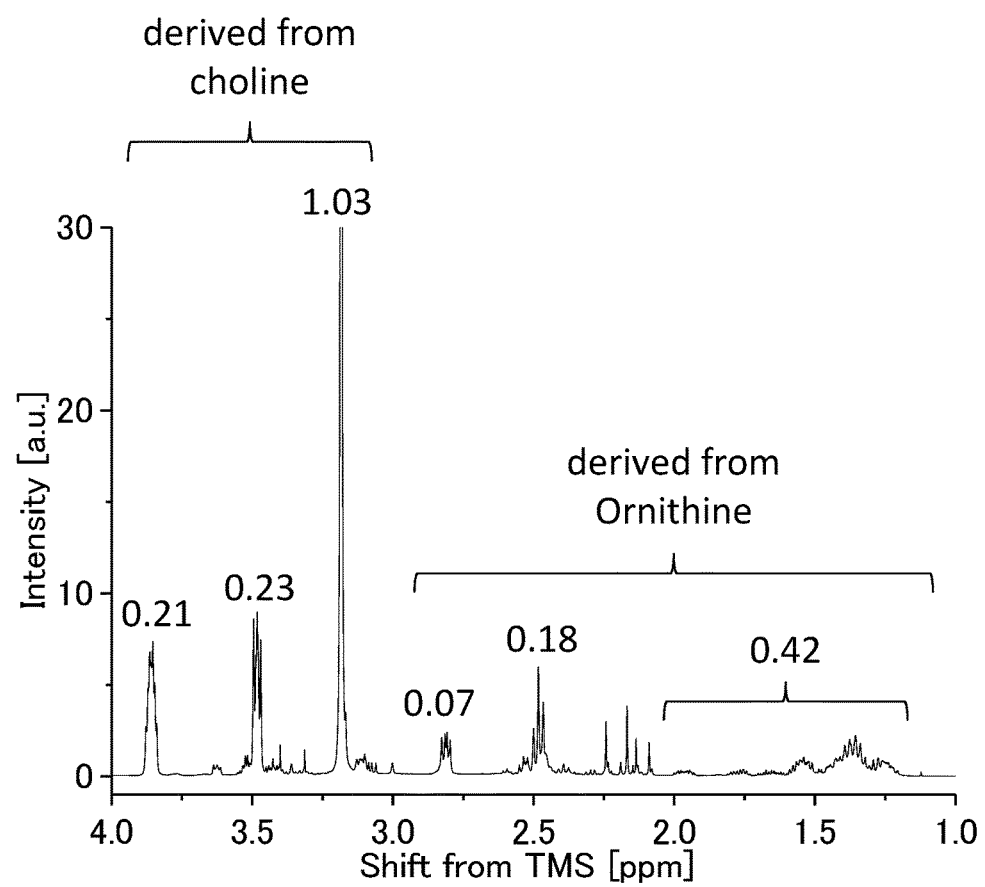
FIG. 10 shows a result of the nuclear magnetic resonance spectrum $^1$H-NMR measurement in the comparative example 2B.

In the comparative example 2B, an experiment similar to the inventive example 2A was conducted, except that the weight of the ornithine was 7.0 grams (approximately, 42 millimoles). FIG. 10 shows a result of the nuclear magnetic resonance spectrum $^1$H-NMR measurement in the comparative example 2B. The value of RCA calculated on the basis of FIG. 10 was 1.20. In the comparative example 2B, the cellulose was not dissolved, even after one hundred hours elapsed from the mixture of the ionic liquid composition and the cellulose.

Comparative Example 2C

In the comparative example 2C, an experiment similar to the inventive example 2A was conducted, except that the ionic liquid composition (0.97 grams) according to the inventive example 2A further contained water (0.078 grams, 8.3 weight percent) and except of using bleached pulp made from wood (average molecular weight: approximately 300,000-500,000) in place of the cellulose Avicel PH-101. In the comparative example 2C, the cellulose was not dissolved, even after one hundred hours elapsed from the mixture of the ionic liquid composition and the cellulose (i.e., bleached pulp).

Comparative Example 2D

In the comparative example 2D, an experiment similar to the comparative example 1D was conducted, except that the choline aqueous solution had a weight of 27.2 grams (110 millimoles) and that ornithine (10.1 grams, 60 millimoles) was used in place of lysine. Also in the comparative example 2D, the cellulose was not dissolved, even after forty-eight hours elapsed from the mixture of the ionic liquid composition and the cellulose.

The following Table 3 shows the results of the above inventive example 2A-the comparative example 2D.

TABLE 3

(Composition: [Ch][Orn])

| | The value of RCA | Water Amount | Results |
|---|---|---|---|
| Comparative Example 2A | 0.81 | 1.5% | Not dissolved even after 100 hours elapsed from the mixture |
| Inventive Example 2B | 0.89 | 1.6% | Dissolved after 5 hours elapsed from mixture |
| Inventive Example 2A | 0.99 | 1.3% | Dissolved after 5 hours elapsed from mixture |
| Inventive Example 2C | 1.14 | 1.9% | Dissolved after 5 hours elapsed from mixture |
| Comparative Example 2B | 1.20 | 1.7% | Not dissolved even after 100 hours elapsed from the mixture |
| Inventive Example 2D | 0.99 | 1.3% | Dissolved after 20 hours elapsed from mixture |
| Inventive Example 2E | 0.99 | 4.3% | Dissolved after 20 hours elapsed from mixture |
| Inventive Example 2F | 0.99 | 6.3% | Dissolved after 30 hours elapsed from mixture |
| Inventive Example 2G | 0.99 | 7.3% | Dissolved after 40 hours elapsed from mixture |
| Comparative Example 2C | 0.99 | 8.3% | Not dissolved even after 100 hours elapsed from the mixture |
| Comparative Example 2D | 0.96 | 10.6% | Not dissolved even after 100 hours elapsed from the mixture |

The value of RCA: molar ratio of [Ch]/[Orn]
Water Amount: the value calculated in accordance with Karl Fischer's method, and defined according to water weight/ionic liquid composition weight As is clear from Table 3, if the value of RCA is not less than 0.89 and not more than 1.14, the cellulose was dissolved in the ionic liquid composition within 40 hours after the mixture of the ionic liquid composition and the cellulose. On the other hand, if the value of RCA is not more than 0.81 or not less than 1.20, the cellulose is not dissolved in the ionic liquid composition even after 100 hours.

Furthermore, if the water amount is not more than 7.3%, the cellulose was dissolved in the ionic liquid composition within 40 hours after the mixture of the ionic liquid composition and the cellulose. On the other hand, if the water amount is not less than 8.3%, the cellulose was not dissolved in the ionic liquid composition even after 100 hours.

It is obvious that a cellulose-degrading enzyme was not used in this experiment.

Inventive Example 2H

In the inventive example 2H, dimethyl sulfoxide (hereinafter, referred to as "DMSO", 1.00 gram, the weight ratio thereof to the ionic liquid [Ch][Orn]: 103%) was added to the cellulose solution (1.00 gram) provided in the example 2A. Then, this solution was left at rest at a temperature of 90 degrees Celsius at normal pressures for 48 hours. The present inventors visually observed whether or not the cellulose and the DMSO were dissolved in each other.

Inventive Example 2I

In the inventive example 2I, an experiment similar to the inventive example 2H was conducted, except of addition of 2.00 grams of DMSO (the weight ratio thereof to the ionic liquid [Ch][Orn]: 206%)

Inventive Example 2J

In the inventive example 2J, an experiment similar to the inventive example 2H was conducted, except of addition of 3.00 grams of DMSO (the weight ratio thereof to the ionic liquid [Ch][Orn]: 309%)

Comparative Example 2E

In the comparative example 2E, an experiment similar to the inventive example 2H was conducted, except of addition of 4.00 grams of DMSO (the weight ratio thereof to the ionic liquid [Ch][Orn]: 412%)

The following Table 4 shows the results of the above inventive example 2H-the comparative example 2E.

TABLE 4

| | Weight ratio of DMSO to [Ch][Orn] [%] | Result |
|---|---|---|
| Inventive Example 2H | 103 | Dissolved in each other |
| Inventive Example 2I | 206 | Dissolved in each other |
| Inventive Example 2J | 309 | Dissolved in each other |
| Comparative example 2E | 412 | Cellulose was precipitated |

As is clear from Table 4, if the weight ratio of the DMSO to the ionic liquid represented by [Ch][Orn] is not more than 309%, the DMSO and the ionic liquid were dissolved in each other within 48 hours. On the other hand, if the weight ratio of the DMSO is not less than 412%, the cellulose was precipitated within 48 hours.

INDUSTRIAL APPLICABILITY

The present invention provides an ionic liquid composition capable of dissolving cellulose without a cellulose-degrading enzyme, namely, an enzyme capable of hydrolyzing cellulose.

The invention claimed is:
1. A solution in which cellulose has been dissolved in an ionic liquid composition, wherein the ionic liquid composition contains:
an ionic liquid; and
water,
wherein
the ionic liquid composition does not contain an enzyme capable of hydrolyzing cellulose;
the ionic liquid is represented by the following chemical formula (I):

$$[(CH_3)_3N(CH_2)_2OH]^+[NH_2\text{-L-CHNH}_2\text{—COO}]^- \quad (I)$$

where
L is absent or a linker;
a molar ratio of $[(CH_3)_3N(CH_2)_2OH]^+$ to $[NH_2$-L-$CHNH_2$—$COO]^-$ is not less than 0.87 and not more than 1.14; and
a weight ratio of the water to the ionic liquid composition is not more than 7.3%.

2. The solution ionic liquid composition according to claim 1, wherein
the molar ratio of $[(CH_3)_3N(CH_2)_2OH]^+$ to $[NH_2$-L-$CHNH_2$—$COO]^-$ is not less than 0.89 and not more than 1.12.

3. The solution according to claim 1, wherein
L is —$(CH_2)_n$—;
where n is a natural number.

4. The solution according to claim 3, wherein
n is equal to 3 or 4.

5. The solution according to claim 1, wherein
the weight ratio of the water to the ionic liquid composition is not less than 1.3%.

6. The solution according to claim 1, wherein the ionic liquid composition further contains an aprotic polar solvent.

7. The solution according to claim 6, wherein
the aprotic polar solvent is dimethyl sulfoxide.

8. The solution according to claim 7, wherein
a weight ratio of the dimethyl sulfoxide to the ionic liquid is not more than 309%.

9. A method for dissolving cellulose, the method comprising:
(a) adding the cellulose to an ionic liquid composition;
wherein
the ionic liquid composition contains an ionic liquid and water;
the ionic liquid composition does not contain an enzyme capable of hydrolyzing cellulose;
the ionic liquid is represented by the following chemical formula (I):

$$[(CH_3)_3N(CH_2)_2OH]^+[NH_2\text{-}L\text{-}CHNH_2\text{—}COO]^- \quad (I)$$

where
L is absent or a linker;
a molar ratio of $[(CH_3)_3N(CH_2)_2OH]^+$ to $[NH_2$-L-$CHNH_2$—$COO]^-$ is not less than 0.87 and not more than 1.14; and
a weight ratio of the water to the ionic liquid composition is not more than 7.3%.

10. The method according to claim 9, wherein
the molar ratio of $[(CH_3)_3N(CH_2)_2OH]^+$ to $[NH_2$-L-$CHNH_2$—$COO]^-$ is not less than 0.89 and not more than 1.12.

11. The method according to claim 9, wherein
L is —$(CH_2)_n$—;
where n is a natural number.

12. The method according to claim 11, wherein
n is equal to 3 or 4.

13. The method according to claim 9, wherein
the weight ratio of the water to the ionic liquid composition is not less than 1.3%.

14. The method according to claim 9, wherein the ionic liquid composition further contains
an aprotic polar solvent.

15. The method according to claim 14, wherein
the aprotic polar solvent is dimethyl sulfoxide.

16. The method according to claim 15, wherein
a weight ratio of the dimethyl sulfoxide to the ionic liquid is not more than 309%.

17. The method according to claim 9, further comprising:
(b1) heating the ionic liquid composition to which the cellulose has been added to dissolve the cellulose in the ionic liquid composition after the step (a).

18. The method according to claim 9, further comprising:
(b2) leaving the ionic liquid composition to which the cellulose has been added at rest to dissolve the cellulose in the ionic liquid composition after the step (a).

19. The method according to claim 9, further comprising:
(b3) stirring the ionic liquid composition to which the cellulose has been added to dissolve the cellulose in the ionic liquid composition after the step (a).

20. A method for fabricating a cellulose film; the method comprising:
(a) adding cellulose to an ionic liquid composition to prepare a cellulose solution;
(b) applying the cellulose solution on a surface of a substrate to form a film on the surface;
(c) removing the ionic liquid composition from the film using a solvent; and
(d) removing the solvent from the film,
wherein
the ionic liquid composition contains an ionic liquid and water;
the ionic liquid composition does not contain an enzyme capable of hydrolyzing cellulose;
the ionic liquid is represented by the following chemical formula (I):

$$[(CH_3)_3N(CH_2)_2OH]^+[NH_2\text{-}L\text{-}CHNH_2\text{—}COO]^- \quad (I)$$

where
L is absent or a linker;
a molar ratio of $[(CH_3)_3N(CH_2)_2OH]^+$ to $[NH_2$-L-$CHNH_2$—$COO]^-$ is not less than 0.87 and not more than 1.14; and
a weight ratio of the water to the ionic liquid composition is not more than 7.3%.

21. The method according to claim 20, wherein
the molar ratio of $[(CH_3)_3N(CH_2)_2OH]^+$ to $[NH_2$-L-$CHNH_2$—$COO]^-$ is not less than 0.89 and not more than 1.12.

22. The method according to claim 20, wherein
L is —$(CH_2)_n$—;
where n is a natural number.

23. The method according to claim 22, wherein
n is equal to 3 or 4.

24. The method according to claim 20, wherein
the weight ratio of the water to the ionic liquid composition is not less than 1.3%.

25. The method according to claim 20, wherein the ionic liquid composition further contains
an aprotic polar solvent.

26. The method according to claim 25, wherein
the aprotic polar solvent is dimethyl sulfoxide.

27. The method according to claim 26, wherein
a weight ratio of the dimethyl sulfoxide to the ionic liquid is not more than 309%.

28. A solution in which cellulose has been dissolved in an ionic liquid composition, wherein the ionic liquid is represented by the following chemical formula (I):

$$[(CH_3)_3N(CH_2)_2OH]^+\text{to }[NH_2\text{-}L\text{-}CHNH_2\text{—}COO]^- \quad (I)$$

where
L is absent or a linker;
wherein a molar ratio of $[(CH_3)_3N(CH_2)_2OH]^+$ to $[NH_2$-L-$CHNH_2$—$COO]^-$ is not less than 0.87 and not more than 1.14.

* * * * *